United States Patent [19]

Lockhoff et al.

[11] Patent Number: 4,631,272
[45] Date of Patent: Dec. 23, 1986

[54] N-ACYLATED 1-ALKYLAMINO-1-DEOXY-KETOSE DERIVATIVES, A PROCESS FOR THEIR PREPARATION AND THEIR USE

[75] Inventors: Oswald Lockhoff, Cologne; Bernd-Wieland Krüger, Wuppertal; Peter Stadler, Haan; Karl G. Metzger, Wuppertal; Hein-Peter Kroll, Wuppertal; Klaus Schaller, Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 699,712

[22] Filed: Feb. 8, 1985

[30] Foreign Application Priority Data

Feb. 17, 1984 [DE] Fed. Rep. of Germany ....... 3405841

[51] Int. Cl.4 .................. A61K 31/70; C07H 5/06
[52] U.S. Cl. ........................... 514/23; 514/62; 536/18.7; 536/53; 536/22
[58] Field of Search .............. 514/23, 62; 536/18.7, 536/53

[56] References Cited

U.S. PATENT DOCUMENTS 3,005,750 10/1961 Fluck et al. ..................... 536/53

FOREIGN PATENT DOCUMENTS 0039077 12/1972 Japan ........................... 536/18.7
0866734 4/1961 United Kingdom ............ 514/23

Primary Examiner—Johnnie R. Brown
Attorney, Agent, or Firm—Sprung Horn Kramer & Woods

[57] ABSTRACT

Compounds of the formula

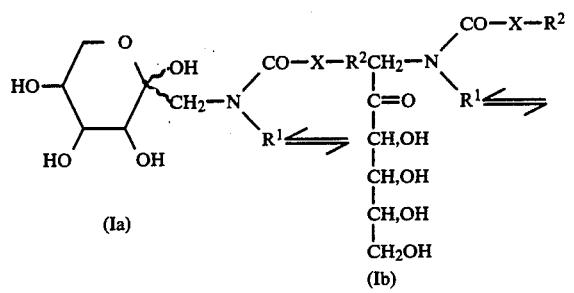

(Ia)

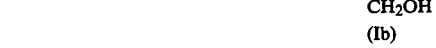

(Ib)

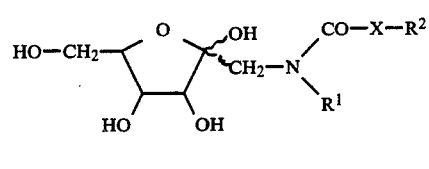

(Ic)

in which $R^1$ represents hydrogen or an optionally substituted, straight-chain or branched alkyl or mono- or poly-unsaturated alkenyl radical with in each case up to 30 C atoms, X represents $CH_2$, O, S or NR, wherein R denotes hydrogen or an alkyl group with up to 20 C atoms, and $R^2$ represents hydrogen or an optionally substituted, straight-chain or branched, saturated or mono- or poly-unsaturated hydrocarbon radical with up to 30 C atoms, or pharmaceutically acceptable salts thereof, stimulate the immune system and help fight infection.

15 Claims, No Drawings

N-ACYLATED 1-ALKYLAMINO-1-DEOXY-KETOSE DERIVATIVES, A PROCESS FOR THEIR PREPARATION AND THEIR USE

The invention relates to new N-acylated 1-alkylamino-1-deoxy-ketose derivatives, a process for their preparation and their use as medicaments.

The new compounds correspond to the formulae Ia to Ic, which are collectively designated formula I below.

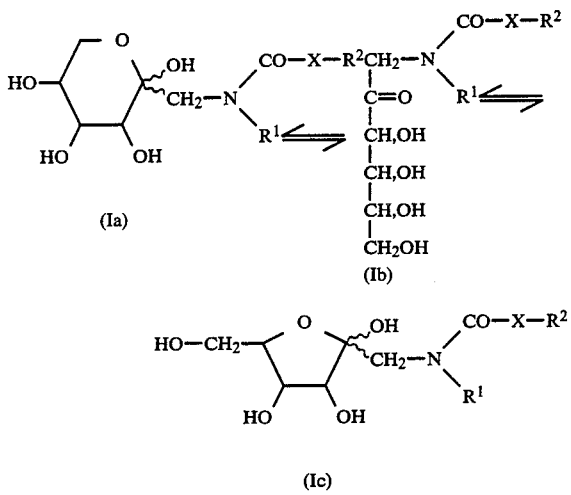

The sugar residue in formula I is an N-substituted 1-amino-1-deoxy-keto-sugar, the keto group being located on carbon atom C-2. This keto function usually forms a cyclic hemi-ketal, including a hydroxyl group. This hemi-ketal is in equilibrium with its open-chain form, but the equilibrium lies clearly on the side of the cyclic form.

If a hemi-ketal is formed with the hydroxyl group located on C-6 of the sugar, an oxygen-containing six-membered ring is formed, as shown in formula Ia. If the hemi-ketal is formed with the hydroxyl group on C-5 of the sugar, an oxygen-containing five-membered ring of the formula Ic is formed. The open-chain form of the sugar has the formula Ib. Since the two cyclic formulae according to formula Ia and formula Ic are in equilibrium with one another and with the open-chain form according to formula Ib, the new compounds are appropriately characterized by the formulae Ia to Ic.

In these formulae:

$R^1$ represents hydrogen or an optionally substituted, straight-chain or branched alkyl or mono- or poly-unsaturated alkenyl radical with in each case up to 30 C atoms, X represents $CH_2$, O, S or NR, wherein R denotes hydrogen or an alkyl group with up to 20 C atoms, and $R^2$ represents hydrogen or an optionally substituted, straight-chain or branched, saturated or mono- or poly-unsaturated hydrocarbon radical with up to 30 C atoms.

$R^1$ preferably represents an alkyl radical with one to 21 carbon atoms, preferably 7 to 21 C atoms. Examples of these radicals $R^1$ which may be mentioned here are: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, docosyl, methyldecyl, methyloctadecyl.

Examples of suitable alkenyl radicals are ethenyl, propen-1-yl, propen-2-yl, i-butenyl, buten-1-yl, buten-2-yl, 1-pentenyl, 2-pentenyl, 3-pentenyl, 4-pentenyl, 1-hexenyl, 2-hexenyl, 3-hexenyl, 4-hexenyl, 5-hexenyl, 1-decenyl, 5-decenyl, 9-decenyl, 8-heptadecenyl, 1,3-butadienyl, 1,3-pentadienyl, 1,4-pentadienyl, 2,4-pentadienyl, 8,11-heptadecanedienyl and 8,11,14-heptadecanetrienyl. The longer-chain, unsaturated radicals are in general preferred, especially the mono- or di-unsaturated alkenyl radicals with 7-21 C atoms.

The unsaturated hydrocarbon radicals can be in the form of pure cis- or trans-isomers or in the form of isomer mixtures.

According to the invention, alkyl and alkenyl radicals $R^1$ are also to be understood as those radicals in which one or more, preferably one or two, methylene or methine groups can be replaced by oxygen, sulphur and/or nitrogen. If the chain is interrupted by nitrogen atoms, this N carries either a hydrogen atom or a $C_1$–$C_{30}$-alkyl radical, preferably a $C_1$–$C_{10}$-alkyl radical, or a —CO—alkyl radical with up to 25, preferably 1 to 10, carbon atoms.

Examples of cases in which the radicals $R_1$ are interrupted by O, S and N or appropriate atom groupings are methoxyethyl, methoxyethoxyethyl, ethylthiododecyl and N-methyl-aminodecyl.

Preferred possible substituents for the radical $R^1$ are the following: aryl, preferably phenyl; halogen, preferably fluorine, chlorine and bromine; amino, $C_1$–$C_6$-alkylamino and di-$C_1$–$C_6$-alkylamino; OH; $C_1$–$C_6$-alkoxy; SH; $C_1$–$C_6$-alkyl—COO and $C_1$–$C_6$-alkyl—CO—NH.

If $R^1$ is substituted, it in general carries 1–5, preferably 1–3, substituents.

Examples of substituted radicals $R^1$ are hydroxyheptadecenyl, aminodecyl, fluoromethyl, β-hydroxytridecyl, mercaptoethyl, phenyltetradeczyl, fluorotetradecyl, fluorohexadecyl, fluorooctadecyl, chlorododecyl, chloropentadecyl, chlorohexadecyl, bromooctadecyl, aminododecyl, aminohexadecyl, ethylamino-hexadecyl, N,N-dihexylaminododecyl, hydroxydodecyl, hydroxytetradecyl, hydroxyhexadedecyl, methoxytetradecyl, butoxytetradecyl, acetyloxyhexadecyl, acetylamidotetradecyl, myristoyloxytetradecyl and myristoylamidohexadecyl.

According to the invention, the hydrocarbon radical $R^2$ can be an alkyl, alkenyl, cycloalkyl, cycloalkenyl or aryl radical, it also being possible for these radicals to occur together, for example as alkylcycloalkyl, aralkyl or alkylaryl.

The radical $R^2$ preferably has 1–20 C atoms. According to the invention, hydrocarbon radicals $R^2$ are also understood as meaning those in which up to 5, preferably one or two, methylene or methine groups are replaced by O, S and/or NR, R representing hydrogen or $C_1$–$C_6$-alkyl, preferably $C_1$–$C_3$-alkyl.

Examples in which $R^2$ represents an alkyl radical or alkenyl radical are those mentioned for $R^1$.

Radicals which may be mentioned in particular are: methyl, propyl, hexyl, decyl, undecyl, dodecyl, tridecyl, tetradecyl, pentadecyl, hexadecyl, heptadecyl, octadecyl, nonadecyl, docosyl, ethylhexyl, isobutyl, propenyl, octenyl, hexadienyl, docosenyl and dimethylhexenyl. The unsaturated hydrocarbon radicals can be in the form of pure cis- or trans-isomers or in the form of an isomer mixture.

Examples of cycloalkyl $R^2$ are cyclopropyl, cyclobutyl, cyclopentyl, cyclohexyl, cycloheptyl and cyclooctyl. The rings with 5, 6 and 7 C atoms are preferred.

Examples of cycloalkenyl radicals $R^2$ are cyclopentenyl, cyclopentadienyl, cyclohexenyl, cyclohexadienyl and cycloheptenyl.

Aryl $R^2$ preferably represents aromatic radicals with 6, 10 or 12 C atoms. Phenyl, naphthyl and the diphenyl radical may be mentioned in particular here.

The radicals $R^2$ can be mono- or poly-substituted, in general mono-, di-, tri-, tetra- or penta-substituted, preferably mono-, di- or tri-substituted. Possible substituents are the substituents mentioned for $R^1$.

Examples of substituted alkyl radicals $R^2$ are methyltetradecyl, hydroxytridecyl, hydroxyoctadecyl, chlorotridecyl, acetyloxytridecyl, myristoyloxytridecyl, aminotridecyl, acetylamidotridecyl and mercaptooctadecyl.

Examples of substituted alkenyl radicals $R^2$ are hydroxytetradecenyl, acetamidooctadecenyl and methoxyheptadecenyl.

Examples of substituted cycloalkyl and cycloalkenyl radicals which may be mentioned are chlorocyclohexyl, methoxycycloheptyl, hydroxycyclohexenyl, acetamidocyclohexenyl.

Examples of substituted aromatic radicals $R^2$ are p-nitrophenyl, 2,4-dichlorophenyl, p-methoxyphenyl, trifluoromethylphenyl and dimethylaminophenyl.

Further examples of radicals $R^2$ in which $CH_2$ or CH groups are replaced as described are the following: ω-(N-ethyl-N-butyl)-aminodedecyl, ω-piperidinyltetradecyl, ω-butoxyoctadecyl and ω-morpholinoheptadecyl.

Finally, the following examples where radicals occur together as $R^2$ may be mentioned: 2-(cyclohexyl)ethyl, benzyl, phenethyl, phenylhexyl, decahydronaphthylethyl and butyldecahydronaphthyl.

If X in formula I represents an N-alkyl group, this alkyl group preferably has 1–10 C atoms.

The compounds of the formula I contain several chiral carbon atoms and are in the form of optically pure diastereomers or in the form of diastereomer mixtures.

Examples of the sugar derivatives described by formula I are thus N-substituted 1-amino-1-deoxy derivatives of psicose, fructose, sorbose or tagatose.

The invention also relates to a process for the preparation of the compounds according to formula I. For this, hexoses, such as, for example, allose, altrose, glucose, mannose, gulose, idose, galactose or talose, either in the free, that is to say unprotected, form or in the form of protected, optionally activated derivatives, are reacted with an amino compound $R^1$—$NH_2$, either in the free form or in the form of a suitable acid addition salt, $R^1$ having the meaning described above. The glycosylamine obtained by this step is rearranged into the N-alkyl-1-amino-1-deoxy-ketoses in a second step, with or without suitable catalysts.

These amino-containing keto-sugars are then reacted with an optionally activated carboxylic acid derivative, thiocarbonic acid derivative, halogenoformic acid ester derivative or isocyanate derivative in a third reaction step, optionally with the addition of bases. Urea derivatives are also obtained by reacting aromatic carbamates with primary or secondary amines. If appropriate, the protective groups present are then split off from the carboxylic acid amides, carbamates, thiocarbamates or ureas thus obtained, to give, in this manner, the compounds of the formula I according to the invention, which, if necessary, can be purified by chromatography, recrystallization, extraction and the like.

In a preferred embodiment of the process according to the invention, the unblocked hexose is reacted with 1 to 10 equivalents of the amine $R^1$—$NH_2$ in question in a first process step in a manner which is known per se in a suitable solvent, if appropriate in the presence of a catalyst, at temperatures between 0° C. and 80° C. High yields of the glycosylamines in question, of the formula II

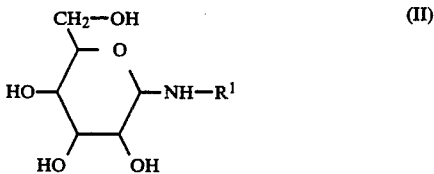

are thereby usually obtained, the products being amorphous or crystalline solids or viscous syrups.

In the second process step, the glycosylamine of the formula II is rearranged into an N-alkylated 1-amino-1-deoxy-ketose of the formula III

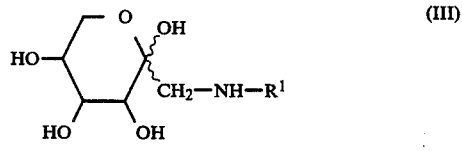

in a suitable solvent, either by prolonged heating without a catalyst or in the presence of an organic or inorganic acid. Rearrangements of this type have been known for a long time and are described in the chemical literature by the name "Amadori rearrangement".

In a third process step, the aminoketose of the formula III is converted into compounds of the formulae Ia–Ic.

If X in formula I represents a methylene group, the corresponding amines of the formula III are reacted with 1 to 10 equivalents of a carboxylic acid derivative of the formula $R^2$—$CH_2$—CO—Y, in which $R^2$ has the abovementioned meaning and Y denotes halogen or a leaving group customary in amidation reactions, preferably an activating ester radical or a group O—CO—$R^2$ with the above meaning for $R^2$, or a group O—CO—O—$R^2$, with the above meaning for $R^2$. The reaction is carried out in organic or aqueous-organic solvents at temperatures between 0° and 50° C., if appropriate in the presence of a base.

If X in formula I represents an oxygen atom, an amine of the formula III is reacted with 1 to 5 equivalents of a halogenocarbonic acid ester Y—CO—O—$R^2$, wherein Y represents halogen, preferably chlorine, and $R^2$ has the meaning described above. The reaction is carried out in organic solvents at a temperature between −20° C. and 50° C., if appropriate in the presence of a base.

If X in formula I denotes an NH group, an amine of the formula III is reacted with 1 to 5 equivalents of an isocyanate $R^2$—NCO, with the abovementioned meaning of $R^2$. The reaction is preferably carried out in organic solvents, if appropriate in the presence of a catalyst, the temperatures being between −20° C. and 50° C.

If X in formula I denotes an NH or N-alkyl group, it is also possible for a carbamate obtained by reacting the amine according to formula II with a preferably aromatic halogenoformic acid ester to be reacted with 1 to 10 equivalents of a primary amine $R^2$—$NH_2$ or secondary amine $R^2$—NH-alkyl, with the meanings for $R^2$ described above. The reaction is preferably carried out at 20° C. to 80° C. in organic solvents.

If X in formula I represents a sulphur atom, an amine of the formula III is reacted with a thiocarbonic acid chloride S-ester $R^2$—S—CO—Y, wherein Y represents halogen, preferably chlorine, and $R^2$ has the above meaning. The reaction is carried out in organic solvents, if appropriate in the presence of a suitable catalyst and/or a base, the reaction temperatures being between 0° and 70° C.

In all the cases described which lead to compounds of the formula I with the abovementioned meanings for X, the reaction product is worked up in the customary manner.

The first process step in the preparation of the compounds of the formula I according to the invention is thus the reaction of a sugar which is unblocked on the anomeric carbon atom with an amine of the type $R^1$—$NH_2$ on the anomeric carbon atom to give the glycosylamine in question, water being split off.

Amines $R^1$—$NH_2$ which are liquid at room temperature can be reacted directly with the sugar, that is to say without a solvent. This reaction is carried out at temperatures between 0° C. and 100° C., preferably at 25° C. to 70° C. Suitable catalysts are mineral acids, such as, for example, hydrochloric acid, sulphuric acid or nitric acid, or short-chain carboxylic acids, such as acetic acid or propionic acid, amounts of 0.001 to 0.5 equivalent being employed.

It is possible in all cases, and also preferred in the case of amines $R^1$—$NH_2$ which are solid at room temperature, to carry out the preparation of the glycosylamines in the presence of a solvent. The reaction is then preferably carried out in the presence of a diluent which is inert under the reaction conditions and in which, preferably, at least either the reactants or the reaction product dissolve.

Possible diluents are alcohols, such as methanol, ethanol, propan-1-ol and propan-2-ol, ethers, such as tetrahydrofuran and dioxane, and also dimethylformamide, the addition of water being preferred, except when alcohols are used. Moreover, in the case of short-chain amines $R^1$—$NH_2$, water is also preferably suitable by itself as the solvent. It may also be advantageous to use the alkanols as a mixture with water.

The reaction temperatures are between −10° C. and 120° C., preferably between 30° C. and 70° C., when solvents are used in the preparation of the glycosylamines.

The diluent in question can be added either before or during the reaction, as desired. In the case of long-chain amines $R^1$—$NH_2$, it is preferably added before the reaction.

The glycosylamines prepared as described above crystallize out either directly or after cooling and can be precipitated or made to crystallize by the addition of suitable auxiliary solvents, preferably auxiliary solvents of low polarity, such as acetone, diethyl ether, cyclohexane, ethyl acetate or petroleum ether, if appropriate with cooling, and, where relevant, the excess amine $R^1$—$NH_2$ present can be removed in a manner which is known per se, by washing or recrystallizing the product.

The second process step comprises rearrangement of the N-substituted glycosylamine of the formula II into the N-substituted 1-amino-1-deoxy-2-ketose of the formula III. This reaction can be carried out with or without a solvent. If no solvent is used, the reaction is carried out at elevated temperature between 50° C. and 150° C., preferably at 100° C. to 120° C., but at least above the melting point of the glycosylamines employed. The yield of the desired rearrangement product of the formula III can be increased by adding mineral acids or organic acids, such as, for example, acetic acid or oxalic acid. The amount of acid varies in the range from 0.0001 to 5.0 molar equivalent, preferably 0.1 to 1.0 molar equivalent, based on the glycosylamine of the formula II.

However, it is in general preferable to carry out the rearrangement in an organic, preferably anhydrous solvent. Examples of suitable solvents are methanol, ethanol, propanol, isopropanol, tetrahydrofuran, dioxane and dimethylformamide. In this variant, it is also advantageous to catalyze the rearrangement by mineral acids or the abovementioned organic acids.

About 0.02 to 0.5 mole of acid is added per mole of aldosylamine of the formula II, and the mixture is warmed for some time, preferably 10 to 100 minutes. The reaction temperatures vary in the range from 40° C. to 150° C., preferably between 60° C. and 90° C.

It is also possible to catalyze the rearrangement in the organic solvent by compounds with active methylene groupings.

Examples of suitable compounds of this type are ethyl malonate, 2,4-pentanedione, phenylacetone, diphenylmethane or malonic acid.

It is furthermore possible, and in some cases also preferable, to combine the abovementioned process steps one and two, that is to say the preparation of the aldosylamine of the formula II and rearrangement thereof into the substituted 1-amino-1-deoxy-2-ketose of the formula III, in one reaction step. In this process variant, the aldose and the amine $R^1$—$NH_2$ are reacted directly, with or without one of the abovementioned solvents, under catalysis by mineral acids or the abovementioned organic acids. This variant is described in the literature (HODGE, Advances in Carbohydrate Chemistry, 10 (1955) 169).

In most cases, the rearrangement of substances of the formula II into substances of the formula III is accompanied by decomposition, to a greater or lesser degree, of the sugar component, this rearrangement being intensified if the heating times are too long or the temperatures or acid concentrations are too high and manifesting itself in the darkening in color of the reaction batch.

Synthesis of the N-substituted 1-amino-1-deoxyketoses of the formula III should therefore in all cases be followed by purification of the reaction batch. The compounds of the formula III are therefore isolated from the batches by the usual purification steps, such as crystallization, extraction, chromatography and the like.

The third process step in the preparation of the compounds of the formula I according to the invention is selective reaction of the N-substituted 1-amino-1-deoxy-2-ketoses of the formula III on the amino function with a carboxylic acid derivative $R^2$—$CH_2$—CO—Y, with the abovementioned meaning of $R^2$ and Y, or with a halogenocarbonic acid ester Y—CO—O—R², with the abovementioned meaning of R² and Y, or with an isocyanate R²—NCO, with the above meaning of R², or with a thiocarbonic acid ester S-chloride R²—S—CO—Y, with the above meaning of R² and Y, or successively with preferably aromatic halogenocarbonic acid esters Y—CO—O—Ar, with the meaning of Y and the aromatic radical descirbed above in the case of R², to give the carbamate, followed by aminolysis with primary or secondary amines R²—NH₂ or R²—NH-alkyl to give the urea derivative.

These carboxylic acid or carbonic acid derivatives are preferably reacted with the 1-amino-1-deoxyketose derivatives in the presence of a diluent in which the reactants are completely or only partly soluble.

Possible diluents are organic or inorganic solvents, preferably those which reduce or prevent side reactions to the greatest possible degree under the reaction conditions. The reaction can be carried out either in organic solvents, such as ethers, for example tetrahydrofuran and dioxane, or alcohols, for example ethanol and propanol, or ketones, for example acetone and methyl ethyl ketone, or in dimethylformamide, ethyl acetate or pyridine, or in mixtures of these solvents with one another and/or with water. The use of anhydrous solvents is in general to be preferred.

1 to 10 equivalents, based on the ketose derivative of the formula III, of the carboxylic acid derivatives R²—CH₂—CO—Y or the carbonic acid derivatives R²—O—CO—Y, R²—NCO and R²—S—CO—Y are employed, the use of 1 to 3 equivalents being preferred.

The acylation reactions can be carried out in the presence of basic auxiliaries. All the usual basic compounds in organic synthesis can be employed, such as, for example, tertiary aliphatic or aromatic amines, or alkali metal or alkaline earth metal hydroxides or carbonates, such as sodium hydroxide solution, sodium carbonate or calcium carbonate, or anion exchanger resins or cation exchanger resins.

The reactions with the carboxylic acid - or carbonic acid derivatives are carried out at temperatures between about −30° C. and +80° C., preferably between −10° C. and +25° C.

The amides, carbamates, ureas or thiocarbamates according to the formula I obtained in this manner are isolated in the form of crystalline or amorphous solids or as syrups by processes which are known per se and, if necessary, are purified by recrystallization, chromatography extraction and the like.

The invention also relates to salts of the compounds of the formula I. These are, above all, usually pharmaceutically useful, non-toxic salts.

The compounds of the invention have a defense-increasing action. It has been found that the class of compounds intensifies the non-specific intrinsic defense of the host. These results have been obtained with the aid of the following experimental design.

DESCRIPTION OF THE EXPERIMENT

Mice of the SPF-CFW1 type were infected intravenously with $2-6\times 10^5$ logarithmically growing cells of *Candida albicans*, suspended in physiological saline solution. Starting with the 3rd day after infection, the first disease symptoms become recognizable in untreated control animals. By the 5th day, the first animals die from acute kidney failure, and by the 14th day after infection as a rule more than 80% of the untreated animals have died. In this test, the compounds of Examples 9, 15, 16 and 28 are found to have a disease-decelerating action. A significant disease-decelerating action was achieved when the substance was administered intraperitoneally (i.p.) in each case once 24 hours before the infection in concentrations of 1–50 mg/kg of body weight.

A statistically significant increase in the survival time of the treated animals in comparison with the untreated controls was observed. About 50% of the treated animals survived an observation period of 14 days, compared with about 20% of the untreated control animals.

The compounds according to the invention can be used by themselves as a prophylactic agent, for the treatment of existing infections, or in combination with an antibiotic therapy, to increase the therapeutic action of antibiotics and chemotherapeutics (for example penicillins, cephalosporins, aminoglycosides and the like) on infected humans and animals.

It has been found that infections of mice with pathogenic germs which lead to the death of the experimental animals within 24–48 hours can be treated prophylactically—preferably intraperitoneally—with 1–80 mg/kg of the compounds according to the invention. This applies to a large number of Gram-positive (for example Staphylococci) and Gram-negative (for example *E. coli*, Klebsiella, Proteus or Pseudomonas) pathogens. This list is by way of example and is in no way to be regarded as a limitation. Thus, for example, 40–100% of mice which have been infected with the pathogenic strain Klebsiella 63 survive this infection after treatment (for example 18hours before infection) with 10–40 mg/kg of the compounds of Examples 9, 13, 15, 24, 27 and 28 according to the invention, while only 0–30% of the untreated control animals survived.

In another experimental model, it was possible to demonstrate that the therapeutic activity of antibiotics can be increased by the compounds according to the invention. Thus, mice were infected with the strain Pseudomonas W. This infection led to death of most of the control animals within 24 hours. Another group was treated with 4 mg/kg of sisomicin 30 hours after infection. It was possible to demonstrate that the therapeutic activity of the sisomicin can be decidedly improved in the experimental group which had been treated with the compounds of Examples 9, 13, 15 and 24 according to the invention 18 hours before infection.

*Salmonella typhimurium* infection of mice

The experimental animals, CFW₁ mice, ♀ ♀, body weight about 20 g, were randomly placed in groups of 10 mice per cage. The groups were treated with in each case 0.5 ml of the substances, formulated in glucose-agar, or with the blank formulation (with no substance) in the control groups, in each case 3 times. The treatment was performed 24 hours and 1 hour before infection and 24 hours after infection. The i.p. infection with *Salmonella typhimurium* strain LT2 and about $5\times 10^5$ germs/mice in 0.25 ml corresponded to an LD₅₀. The course of the infection in the control groups manifested itself by an initial phase of 4 days, in which the animals did not die. This initial phase offers the animals the possibility of activating cellular immune mechanisms and thus simulates the non-specific defense of a latent or chronic infection. From day 4 to 12 after infection, about 50% of the control animals died. After an observation period of 21 days, the experiment was ended. The experiments were evaluated by comparing the control groups with the treated groups. Both the reduced mortality rate and the increase in the initial phase of the infection were used as criteria for the effectiveness of the substances.

The compound of Example 9 both increased the initial phase of the infection and reduced the mortality rate. The effects were observed in the concentration range from 0.1 to 1 mg/kg of body weight. The compound of Example 16 exhibited a dose-dependent reduction of the mortality rate in the concentration range from 1 to 10 mg/kg of body weight.

The new compounds can thus be used to promote defence reactions in humans and animals which are already proceeding subliminally. The compounds are accordingly particularly suitable for stimulation of the endogenous defense, for example in the case of chronic and acute infections, as well as in the case of hereditary or acquired general (that is to say not antigen-specific) immunological defect conditions, such as occur in old age, in the course of serious primary diseases and, in particular, after therapy with ionizing rays or with immuno-suppressant substances. The substances mentioned can thus also preferably be administered in combination with anti-infective antibiotics, chemotherapeutics or other treatments, to counteract immunological damage. Finally, the substances described are also suitable for the general prophylaxis of infectious diseases in humans and animals.

The pharmaceutical products of the present invention are preferably tablets or gelatine capsules, which contain the active compound together with diluents, for example lactose, mannitol, sorbitol or cellulose, and/or lubricants, for example silica, talc or stearic acid or salts thereof, such as magnesium stearate or calcium stearate, and/or polyethylene glycol. Tablets also contain binders, for example magnesium silicate, starches, such as corn starch, wheat starch, rice starch or arrowroot starch, gelatine, tragacanth, methylcellulose, sodium carboxymethylcellulose and/or polyvinylpyrrolidone and, if desired, disintegrating agents, for example starches, agar or alginic acid or a salt thereof, such as sodium alginate, and/or effervescent mixtures, or adsorbents, colorants, flavoring agents and sweeteners. Injectable products are preferably isotonic aqueous solutions or suspensions. Suppositories, ointments or creams are, above all, fatty emulsions or suspensions. The pharmaceutical products can be sterilized and/or can contain auxiliaries, for example preservatives, stabilizers, wetting agents and/or emulsifying agents, solubilizing agents, salts for regulating the osmotic pressure and/or buffers. The present pharmaceutical products, which, if desired, can contain other pharmacologically useful substances, are prepared in a manner which is known per se, for example by means of conventional mixing, granulating or coating processes, and contain from about 0.1% to about 75%, in particular from about 1% to 50%, of the active substances mentioned.

The orally administered products of the present invention can also be provided with a coating which is resistant towards gastric juice.

The compounds according to the invention can be used as defense-increasing and immunopotentiating agents for the treatment of chronic and acute infections (for example bacterial, viral and parasitic). They can also be used as adjuvants in the stimulation of phagocytosis in cases of dysregulation of the defense and immune system.

EXAMPLES

1. 1-Deoxy-1-butylamino-D-fructose oxalate 18 g of D-glucose are suspended in 200 ml of dioxane and 100 ml of ethanol, and 7.3 g of butylamine are added. The mixture is warmed to 70° C. and, after 10 minutes, 9.0 g anhydrous oxalic acid is added. The temperature is maintained for 4 hours. After cooling to room temperature, the product crystallizes out. The solid is filtered off with suction, rinsed five times with 50 ml of ethanol each time and dried in vacuo.

2. 1-Deoxy-1-dodecylamino-D-fructose oxalate

This compound is prepared analogously to Example 1, from 18 g of glucose and 18.5 g of dodecylamine.

3. 1-Deoxy-1-tetradecylamino-D-fructose oxalate

This compound is prepared analogously to Example 1, from 18 g of D-glucose and 21.3 g of tetradecylamine.

4. 1-Deoxy-1-octadecylamino-D-fructose oxalate

This compound is prepared analogously to Example 1, from 18 g of D-glucose and 27 g of stearylamine.

5. 1-Deoxy-1-dodecylamino-D-tagatose oxalate

This compound is prepared analogously to Example 1, from 18 g of D-galactose and 18.5 g of dodecylamine.

6. 1-Deoxy-1-tetradecylamino-D-tagatose oxalate

This compound is prepared analogously to Example 1, from 18 g of D-galactose and 21.3 g of tetradecylamine.

7. 1-Deoxy-1-octadecylamino-D-tagatose oxalate

This compound is prepared analogously to Example 1, from 18 g of D-galactose and 27 g of stearylamine.

8. 1-Deoxy-1-(N-butyl-dodecanoylamido)-D-fructose 5 g of the compound from Example 1 are suspended in 80 ml of tetrahydrofuran, and 4.3 g of dodecanoic acid chloride are added. When the reaction has ended, the solid is filtered off with suction, the filtrate is evaporated to a syrup and the syrup is separated by column chromatography (eluting agent: methylene chloride/methanol 20/1).

Rf value 0.28 in toluene/n-propanol 6/1

$\alpha_D = -15°$ C. (c=1.0 in methylene chloride)

9. 1-Deoxy-1-(N-dodecyl-octadecanoylamido)-D-fructose

This compound is prepared analogously to Example 8, from 6.7 g of the compound from Example 2 and 6.0 g of stearic acid chloride.

Rf value 0.31 in toluene/n-propanol 6/1

$\alpha_D = -8.5°$ (c=1.0 in methylene chloride).

10. 1-Deoxy-1-(N-dodecyl-dodecanoylamido)-D-fructose

This compound is prepared analogously to Example 8, from 6.7 g of the compound from Example 2 and 4.3 g of dodecanoic acid chloride.

$\alpha_D = -11.3°$ (c=1.0 in methylene chloride) 11. 1-Deoxy-1-(N-dodecyl-hexadecanoylamido)-D-fructose This compound is prepared analogously to Example 8, from 6.7 g of the compound from Example 2 and 5.4 g of hexadecanoic acid chloride.

$\alpha_D = -9.3°$ (c=1.1 in methylene chloride)

12.
1-Deoxy-1-(N-tetradecyl-hexadecanoylamido)-D-fructose

This compound is prepared analogously to Example 8, from 7.2 g of the compound from Example 3 and 5.4 g of hexadecanoic acid chloride.

$\alpha_D = -8.7°$ (c=1.05 in methylene chloride)

13.
1-Deoxy-1-(N-tetradecyl-octadecanoylamido)-D-fructose

This compound is prepared analogously to Example 8, from 7.2 g of the compound from Example 3 and 6.0 g of octadecanoic acid chloride.

$\alpha_D = -4.6°$ (c=1.05 in methylene chloride)

14. 1-Deoxy-1-(N-tetradecyl-oleylamido)-D-fructose

This compound is prepared analogously to Example 8, from 7.2 g of the compound from Example 3 and 6.0 g of oleic acid chloride.

$\alpha_D = -4.7°$ (c=1.80 in methylene chloride)

15.
1-Deoxy-1-(N-octadecyl-dodecanoylamido)-D-fructose

This compound is prepared analogously to Example 8, from 8.0 g of the compound from Example 4 and 4.3 g of dodecanoic acid chloride.

$\alpha_D = -5.6°$ (c=2.04 in methylene chloride)

16.
1-Deoxy-1-(N-octadecyl-octadecanoylamido)-D-fructose

This compound is prepared analogously to Example 8, from 8.0 g of the compound from Example 4 and 6.0 g of octadecanoic acid chloride $\alpha_D = -2.8°$ (c=0.95 in methylene chloride)

17.
1-Deoxy-1-(N-tetradecyl-N-dodecyloxycarbonyl)-amino-D-fructose

This compound is prepared analogously to Example 8, from 7.2 g of the compound from Example 3 and 4.7 g of dodecyl chloroformate.

$\alpha_D = -6.9°$ (c=0.85 in methylene chloride)

18.
1-Deoxy-1-(N-tetradecyl-N-octadecyloxycarbonyl)-amino-D-fructose

This compound is prepared analogously to Example 8, from 7.2 g of the compound from Example 3 and 6.4 g of octadecyl chloroformate.

$\alpha_D = -3.2°$ (c=1.15 in methylene chloride)

19.
1-Deoxy-1-(N-octadecyloxycarbonyl)-amino-D-fructose

This compound is prepared analogously to Example 8, from 8.0 g of the compound from Example 4 and 6.4 g of octadecyl chloroformate.

$\alpha_D = -2.6°$ (c=0.95 in methylene chloride)

20.
1-Deoxy-1-[N-dodecyl-N-(dodecylamino-carbonyl)]-amino-D-fructose

This compound is prepared analogously to Example 8, from 6.7 g of the compound from Example 2 and 3.9 g of dodecyl isocyanate.

$\alpha_D = -4.6°$ (c=1.20 in methylene chloride)

21.
1-Deoxy-1-[N-dodecyl-N-(octadecylaminocarbonyl)]-amino-D-fructose

This compound is prepared analogously to Example 8, from 6.7 g of the compound from Example 2 and 5.6 g of octadecyl isocyanate.

$\alpha_D = -3.8°$ (c=1.0 in methylene chloride)

22.
1-Deoxy-1-[N-octadecyl-N-(dodecylaminocarbonyl)]-amino-D-fructose

This compound is prepared analogously to Example 2, from 8.0 g of the compound from Example 4 and 3.9 g of dodecyl isocyanate $\alpha_D = -4.3°$ (c=1.05 in methylene chloride)

23.
1-Deoxy-1-[N-octadecyl-N-(octadecylaminocarbonyl)]-amino-D-fructose

This compound is prepared analogously to Example 8, from 8 g of the compound from Example 4 and 5.6 g of octadecyl isocyanate.

$\alpha_D = -1.9°$ (c=0.83 in methylene chloride)

24.
1-Deoxy-1-(N-dodecyl-dodecanoylamido)-D-tagatose

This compound is prepared analogously to Example 8, from 6.7 g of the compound from Example 5 and 4.3 g of dodecanoic acid chloride.

$\alpha_D = -10.4°$ (c=0.56 in methylene chloride)

25.
1-Deoxy-1-(N-dodecyl-octadecanoylamido)-D-tagatose

This compound is prepared analogously to Example 8, from 6.7 g of the compound from Example 5 and 6.0 g of octadecanoic acid chloride.

$\alpha_D = -3.6°$ (c=0.95 in methylene chloride)

26.
1-Deoxy-1-(N-tetradecyl-octadecanoylamido)-D-tagatose

This compound is prepared analogously to Example 8, from 7.2 g of the compound from Example 6 and 5.0 g of octadecanoic acid chloride.

$\alpha_D = -3.4°$ (c=1.0 in methylene chloride)

27.
1-Deoxy-1-(N-octadecyl-dodecanoylamido)-D-tagatose

This compound is prepared analogously to Example 8, from 8.0 g of the compound from Example 7 and 4.3 g of dodecanoic acid chloride.

$\alpha_D = -3.6°$ (c=1.1 in methylene chloride)

28.
1-Deoxy-1-(N-octadecyl-octadecanoylamido)-D-tagatose

This compound is prepared analogously to Example 8, from 8.0 g of the compound from Example 7 and 6.0 g of octadecanoic acid chloride.

$\alpha_D = -3.4°$ (c=0.85 in methylene chloride

29.
1-Deoxy-1-(N-octadecyl-N-tetradecyloxycarbonyl)-amino-D-tagatose

This compound is prepared analogously to Example 8, from 8.0 g of the compound from Example 7 and 5.2 g of tetradecyl chloroformate.

$\alpha_D = -3.8°$ (c=1.8 in methylene chloride)

30.
1-Deoxy-1-(N-octadecyl-N-octadecylamino-carbonyl)-amino-D-tagatose

This compound is prepared analogously to Example 8, from 8.0 g of the compound from Example 7 and 5.6 g of octadecyl isocyanate.

$\alpha_D = -3.2°$ (c=1.0 in methylene chloride)

31. 1-Deoxy-1-[N-dodecyl-N-(4-tert.-butylcyclohexyloxycarbonyl)]-amino-D-fructose This compound is prepared analogously to Example 8, from 6.7 g of the compound from Example 2 and 4.4 g of 4-tert.-butylcyclohexyl chloroformate.

$\alpha_D = -1.9°$ (c=1.05 in methylene chloride)

32.
1-Deoxy-1-[N-octadecyl-N-(4-tert.-butyl-cyclohexyloxycarbonyl)]-amino-D-fructose This compound is prepared analogously to Example 8, from 8.0 g of the compound from Example 4 and 4.4 g of 4-tert.-butylcyclohexyl chloroformate.

$\alpha_D = -2.2°$ (c=1.05 in methylene chloride)

It is understood that the specification and examples are illustrative but not limitative of the present invention and that other embodiments within the spirit and scope of the invention will suggest themselves to those skilled in the art.

We claim:

1. A compound of the formulae Ia to Ic in which
R¹ represents hydrogen or a straight-chain or branched alkyl or mono or poly-unsaturated alkenyl radical with in each case up to 30 carbon atoms and optionally substituted by phenyl, halogen, amino, $C_1$-$C_6$-alkylamino, di-$C_1$-$C_6$-alkylamino, OH, $C_1$-$C_6$-alkoxy, SH, $C_1$-$C_6$-alkyl—COO and $C_1$-$C_6$-alkyl—CO—NH,
X represents $CH_2$, O, S or NR, wherein
R denotes hydrogen or an alkyl group with up to 20 carbon atoms, and
R² represents hydrogen or a straight-chain or branched, saturated or mono- or poly-unsaturated hydrocarbon radical with up to 30 carbon atoms and optionally substituted by phenyl, halogen, amino, $C_1$-$C_6$-alkylamino, di-$C_1$-$C_6$-alkylamino, OH, $C_1$-$C_6$-alkoxy, SH, $C_1$-$C_6$-alkyl—COO and $C_1$-$C_6$-alkyl—CO—NH, or a pharmaceutically acceptable salt thereof.

2. A compound or salt according to claim 1, in which
R¹ represents an optionally substituted straight-chain or branched alkyl radical with 7–21 carbon atoms or a mono- or di-unsaturated straight-chain or branched alkenyl radical with 7–21 carbon atoms and optionally substituted by phenyl, halogen, amino, $C_1$-$C_6$-alkylamino, di-$C_1$-$C_6$-alkylamino, OH, $C_1$-$C_6$-alkoxy, SH, $C_1$-$C_6$-alkyl—COO and $C_1$-$C_6$-alkyl —CO—NH.

3. A compound or salt according to claim 1, in which R² has 1–20 carbon atoms.

4. A compound according to claim 1, wherein the compound is 1-deoxy-1-(N-dodecyl-octadecanoylamido)-D-fructose or a pharmaceutically acceptable salt thereof.

5. A compound according to claim 1, wherein the compound is 1-deoxy-1-(N-tetradecyl-octadecanoylamido)-D-fructose or a pharmaceutically acceptable salt thereof.

6. A compound according to claim 1, wherein the compound is 1-deoxy-1-(N-octadecyl-dodecanoylamido)-D-fructose or a pharmaceutically acceptable salt thereof.

7. A compound according to claim 1, wherein the compound is 1-deoxy-1-(N-octadecyl-octadecanoylamido)-D-fructose or a pharmaceutically acceptable salt thereof.

8. A compound according to claim 1, wherein the compound is 1-deoxy-1-(N-dodecyl-dodecanoylamido)-D-tagatose or a pharmaceutically acceptable salt thereof.

9. A compound according to claim 1, wherein the compound is 1-deoxy-1-(N-octadecyl-dodecanoylamido)-D-tagatose or a pharmaceutically acceptable salt thereof.

10. A compound according to claim 1, wherein the compound is 1-deoxy-1-(N-octadecyl-octadecanoylamido)-D-tagatose or a pharmaceutically acceptable salt thereof, 11. An immunostimulating composition comprising an immunostimulating effective amount of a compound or salt according to claim 1 in admixture with a diluent.

12. A unit dose of a composition according to claim 1 in admixture with a diluent.

13. A method of stimulating the immune system of an animal which comprises administering to such animal an immunostimulating effective amount of a compound or salt according to claim 1.

14. The method according to claim 13, wherein such compound is selected from the group consisting of
1-deoxy-1-(N-dodecyl-octadecanoylamido)-D-fructose,
1-deoxy-1-(N-tetradecyl-octadecanoylamido)-D-fructose,
1-deoxy-1-(N-octadecyl-dodecanoylamido)-D-fructose,
1-deoxy-1-(N-octadecyl-octadecanoylamido)-D-fructose,
1-deoxy-1-(N-dodecyl-dodecanoylamido)-D-tagatose, 1-deoxy-1-(N-octadecyl-dodecanoylamido)-D-tagatose
or 1-deoxy-1-(N-octadecyl-octadecanoylamido)-D-tagatose or a pharmaceutically acceptable salt thereof.

15. Process for the preparation of the compounds according to claim 1, comprising (a) reacting a hexose with an amino compound of the formula $R^1$—$NH_2$, to give a glycosylamino of the formula II

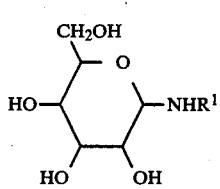

(b) rearranging the glycosylamine II into an N-alkylisated 1-amino-1-deoxyketose of the formula III

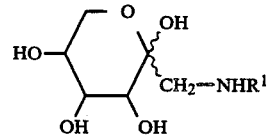

by the procedure of an Amadori rearrangement, and (c) introducing the group —COX—$R^2$ into the compounds III with a reagent selected from the group consisting of $R^2$—$CH_2$—CO—Y, Y—CO—O—$R^2$, $R^2$—NCO, an aromatic halogenoformic acid ester plus a primary amine $R^2$—$NH_2$ or secondary amine $R^2$—NH-alkyl and $R^2$—S—CO—Y, Y being selected from the group consisting of halogen, O—CO—$R^2$ and O—CO—O—$R^2$, wherein $R^1$, $R^2$ and X are as defined in claim 1.

* * * * *